United States Patent
Portney

(10) Patent No.: US 8,894,706 B2
(45) Date of Patent: Nov. 25, 2014

(54) NON-PROLATE BI-SIGN ASPHERIC INTRAOCULAR LENS

(75) Inventor: Valdemar Portney, Newport Coast, CA (US)

(73) Assignee: Aaren Scientific Inc., Ontario, CA (US)

( * ) Notice: Subject to any disclaimer, the term of this patent is extended or adjusted under 35 U.S.C. 154(b) by 570 days.

(21) Appl. No.: 12/415,742

(22) Filed: Mar. 31, 2009

(65) Prior Publication Data

US 2010/0234943 A1   Sep. 16, 2010

Related U.S. Application Data

(60) Provisional application No. 61/159,369, filed on Mar. 11, 2009.

(51) Int. Cl.
*A61F 2/16* (2006.01)

(52) U.S. Cl.
CPC ......... *A61F 2/1618* (2013.01); *A61F 2002/164* (2013.01); *A61F 2/1654* (2013.01)
USPC ......................................... 623/6.24; 623/6.23

(58) Field of Classification Search
USPC .............................. 623/6.23–6.24, 6.27–6.29
See application file for complete search history.

(56) References Cited

U.S. PATENT DOCUMENTS

| | | |
|---|---|---|
| 4,504,982 A | 3/1985 | Burk |
| 5,800,532 A | 9/1998 | Lieberman |
| 6,007,747 A | 12/1999 | Blake et al. |
| 6,015,435 A | 1/2000 | Valunin et al. |
| 6,457,826 B1 | 10/2002 | Lett |
| 6,814,439 B2 | 11/2004 | Portney |
| 7,350,918 B2 | 4/2008 | Clough et al. |
| 7,381,221 B2 | 6/2008 | Lang et al. |
| 7,556,375 B2 * | 7/2009 | Caroline et al. ......... 351/159.33 |
| 2001/0051826 A1 * | 12/2001 | Bogaert et al. ............... 623/6.23 |
| 2004/0106992 A1 * | 6/2004 | Lang et al. .................... 623/6.28 |
| 2006/0116764 A1 * | 6/2006 | Simpson ....................... 623/6.23 |
| 2006/0279697 A1 * | 12/2006 | Clough et al. ................ 351/177 |

* cited by examiner

*Primary Examiner* — David H Willse
*Assistant Examiner* — Tiffany Shipmon
(74) *Attorney, Agent, or Firm* — Hackler Daghighian & Martino

(57) ABSTRACT

An intraocular lens for implantation into a human eye is described. The lens has at least one aspheric surface configured with non-prolate profile to maintain lens optical advantage as compared with equivalent power spherical lens within realistic clinical condition of lens tilt and decentration.

21 Claims, 5 Drawing Sheets

NON-PROLATE BI-SIGN ASPHERIC INTRAOCULAR LENS

The present application claims priority from U.S. Ser. No. 61/159,369 filed Mar. 11, 2009. This application is to be incorporated herewith in its entirety by this specific reference thereto.

FIELD OF THE INVENTION

This invention relates to intraocular lens and more specifically to an improved intraocular lens.

BACKGROUND OF THE INVENTION

Intraocular lenses or IOLs are routinely used in most cataract surgery cases to correct aphakia. They are called Aphakic IOLs. IOLs are also used in the refractive surgery to correct refractive error of phakic subjects. These lenses are called Phakic IOLs or PIOLs. Another type of IOLs is toric IOL which includes torix, i.e. surface with cylinder power, on one of its surfaces. More recently a multifocal optic was introduced and the corresponding lenses are called Multifocal IOLs or MIOLs. The term IOL is used in reference to all above types of intraocular lenses through out the text below.

The average pupil size of the eye at normal photopic lighting condition is around 3 mm diameter and increases or dilates to about 5 mm diameter or even higher al low light condition called mesopic condition. Changes in pupil size contribute to imaging quality of the eye—the image quality usually reduces with pupil dilation. In addition to pupil size the lens decentration (radial translation) or tilt (axial rotation), jointly called misalignments, significantly contribute to the image quality also. A dioptric power of the intraocular lens is selected for the implantation per photopic conditions, i.e. average pupil size of about 3 mm. Fortunately, with present day surgical technique, common lens misalignment does not practically impact the image quality for up to about 4 mm pupil diameter but then the issue arises with the pupil dilation above 4 mm diameter which usually occurs with the reduction in lighting.

The final quality of the retinal image in patients with IOLs depends upon the aberrations of the eye. Even in the perfectly centered position of spherical IOL, there is still spherical aberration. Burk in the U.S. Pat. No. 4,504,982 was first who addressed this type of aberration. He suggested an aspheric lens that had a plurality of radii from the apex to the edge with the radii generally increasing away from the apex. This aspheric lens eliminates most of the spherical aberrations occurred in the lens centered position by the use of the progressively longer radii towards the outer zone of the lens. Among aphakic lenses, Tecnis® IOL was one of the first commonly utilized aspheric IOL that relies on the above principle. As it was reported by J. T. Holliday, et al., "A New Intraocular Lens Designed to Reduce Spherical Aberration of Pseudophakic Eyes," Journal of Refractive Surgery 2002, the Tecnis® IOL has been found to improve visual contrast sensitivity at dilated pupils.

The Tecnis® Z9000 IOL was designed to correct the average corneal spherical aberrations present in the cataract population and mathematically defined as prolate elliptical surface with corneal asphericity Q=−0.26. However, Tecnis® type lenses generally require precise positioning in the capsular bag to provide improved optical quality over a spherical IOL, see "Prospective Randomized Trial of an Anterior Surface Modified Prolate Intraocular Lens," Journal of Refractive surgery, Vo. 18, November/December 2002. Slight lens misalignment greatly reduces the effectiveness of the lens with dilated pupils.

In order to manage to some degree imaging sensitivity to lens misalignment, AcrySol® lens was introduced with only partial corneal spherical aberration compensation. Nevertheless, tilt or decentration with either this lens or Tecnis® type lens can still lead to significant distortions that will be worse than they may have demonstrated by a conventional spherical lens.

The described above aspherization was further expanded in the US Application No. 20060116764 where the aspherization was incorporated into the base profile over which diffractive echelettes are superimposed on in order to improve image contrast over the lens with spherical base profile of the equivalent power. In order to achieve image contrast improvement by base profile aspherization the diffractive zone with the corresponding aspheric base profile, must be above approximately 4 mm diameter because below about 4 mm diameter a spherical base profile incorporates only small magnitude of aberrations and thus provides close to diffractive-limited performance for an equivalent aspheric monofocal lens. Thus, base surface profile aspherization as described in the above disclosure, technically makes sense only for full aperture diffractive optic occupying above 4 mm diameter where image contrast improvement can be achieved. It will be shown in the invention description below that one can achieve improvement in contrast over corresponding spherical base profile even in case of partial surface diffractive zone occupying below of about 4 mm diameter if both base profile and surface periphery outside the diffractive zone are aspherized or even if only surface periphery is properly aspherized.

The SofPort® Advanced Optics (AO) aberration-free aspheric intraocular lens was also introduced. The lens was designed so that the lens itself had no spherical aberration. Though it reduced sensitivity to lens misalignment, its image quality in close to centered lens position was not much differ from one offered by conventional spherical lens of the equivalent power.

The common design of the aspheric IOLs that only target spherical aberration is their prolate surface shape, i.e. the shape is such that the radii generally increasing away from the apex (surface vertex) as originally suggested by Burk.

It is believed that "typical" magnitude of IOL misalignment is less than about 1.0 mm decentration and less than about 10 degrees tilt, these is so called "realistic clinical condition". Therefore, a benefit of aspheric prolate surface lenses that are designed to compensate only for spherical aberration is limited because the imaging quality of such lenses may reduce below the imaging quality of the equivalent power spherical lens within the realistic clinical condition.

Lang et al in U.S. Pat. No. 7,381,221 introduced a multizonal monofocal ophthalmic lens that is designed to be less sensitive to lens decentration. The proposed lens is designed as a combination of prolate zones with different asphericities and powers. The lens was designed to compensate for some effect of decentration that results in a shift in focus position but doesn't address a possible lens tilt or a combination of tilt and decentration which is more common clinically.

Thus, there is the need for a better solution for aspheric optic that would maintain the imaging superiority over conventions spherical lens of the equivalent power within the realistic clinical condition.

In order to explain the invention the following background information is also provided.

It has been a common approach to describe aspheric lens aberrations in terms of wavefront aberrations. Wavefront Error can be represented mathematically as Zernike Polynomial Decomposition $W(\rho,\theta)=\Sigma a_{n,m}Z_n^m(\rho,\theta)$, where $Z_n^m(\rho,\theta)$ are Zernike radial polynomials of n-order and m-frequency and $a_{n,m}$ are Zernike Coefficients as the measure of wavefront aberrations and commonly called "aberrations". In this Zernike Polynomial Decomposition, $2^{nd}$ order aberrations are called Low Order Aberrations (LOA) which includes defocus and astigmatism, and aberrations above $2^{nd}$ order are called High Order Aberrations (HOA). They include spherical aberration, coma, trefold, etc.

There is certain misconception about wavefront aberrations as applied to ocular imaging because they are mathematical abstraction and do not directly represent light distribution at the retina in a form of spot diagram. Their impact on the image quality can only be measured through their relationship with ray aberrations which directly relate to the light distribution at the retinal image.

The key benefit of wavefront aberrations lies in the ability to assess a relative contribution on the optical quality by different wavefront aberrations. This is because Zernike radial polynomials are normalized orthogonal set of functions and their coefficients which are called "wavefront aberration", can be easily combined into groups by Root Mean Square (RMS) per formula $RMS^2=\Sigma(a_{n,m})^2$. For instance, one can combine Low Order Aberration into $RMS_{LOA}$ and high order aberrations into $RMS_{HOA}$ in order to assess their relative contributions to the optical quality. Low order wavefront aberrations are related to ray aberrations such as defocus and astigmatism jointly called refractive error which is correctable by conventional optical aids such as glasses, contact lenses and IOLs, but high order aberrations generally are not.

In order to understand a relationship between the aberrations and light distribution at the retina, optically called spot diagram, one has to include ray aberrations. The relationship between wavefront and ray aberrations can be found for instance in James C Wyant, "Basic Wavefront Aberration Theory for Optical Metrology", Applied Optics and Optical Engineering, Vol. XI, Chapter 1, 1992.

Wavefront error is usually defined at the Entrance Pupil of the optical system as W(x,y), where x, y are pupil Cartesian coordinates. Assuming the wavefront error W(x,y) is relatively small and the angle between the reference and aberrated wavefronts is also small, FIG. 2. This angle $\alpha_x$ is called angular aberration of the ray and defined by the first derivative of the wavefront error $$\alpha_x = \frac{-\partial W(x,y)}{n\partial x}.$$

The corresponding transverse aberration $T_x$ and longitudinal aberration L of the ray are also defined by the first derivative of the wavefront aberration:

$$T_x = R_w\alpha_x = -R_w\frac{\partial W(x,y)}{n\partial x};$$

the same for $T_y$; as transverse ray aberrations along x and y-coordinates at the pupil. The ratio of the longitudinal ray aberration and transverse ray aberration and $$\frac{L}{T_x} \approx \frac{R_w}{(x-T_x)} \approx \frac{R_w}{x}$$

and $$L \approx -\frac{R_w^2}{x}\frac{\partial W(x,y)}{n\partial x}.$$

It is resulted in the difference between the distances to the aberrated ray focus and perfect ray focus where foci are defined as the points of intersections of these rays with the optical axis.

Thus, wavefront aberrations have abstract mathematical meaning of the coefficients in Zernike Polynomial Decomposition but at certain low enough orders of the wavefront aberrations such defocus, astigmatism, spherical aberration and coma, they correlate per above equations with the ray aberrations under the same names. Ray aberrations have physical meaning of light energy travel and can be geometrically interpreted by light rays distribution at the retina. This allows to describing the invention in geometrical terms which are more perceptible than abstract mathematical terms of wavefront aberrations.

In summary, there are two measures of vision quality: (1) pupil based which are wavefront related such as wavefront aberrations and RMS because wavefront is defined at the pupil plane of the eye, and (2) image plane based such as PSF (Point Spread Function), Strehl Ratio and MTF related which are derived from the spot diagram at the image plane, i.e. an image of the point object at the retina. Aberrometry used for measuring eye aberrations directly measures spot diagram and derives all other measures from it.

Pupil based measures are in good correlation with vision quality for 3 mm pupil and smaller because the aberrations are only small fraction of the wavelength. At this condition of the nominal eye is almost diffractive limited system and its Strehl Raito is 0.8 or higher. At this condition there is a linear relationship between Strehl Ratio and $(RMS^2)$, i.e. pupil based measure lineally relates to pupil based measure and one can use either one for image quality analysis.

It has been shown that for larger pupils with large aberrations, pupil based measures are in poor correlation with vision quality and image plane based measures are much better to use in these conditions. At very large aberrations, spot diagram size becomes a dominant factor. Thus, it is more appropriate to utilize spot diagram and corresponding ray aberrations for image quality analysis at large pupil and lens misalignment where the aberrations are significant.

The simplest ray aberration to interpret is longitudinal ray aberration as being one-dimensional characteristic as the transverse (tangential) ray aberration is defined by two-dimensional characteristic. For optically centered system, longitudinal ray aberration is also called longitudinal spherical aberration or LSA. One can divide the entrance pupil or lens surface along, say x-meridian, into the regions. Each region can be characterized by its own longitudinal spherical aberration and the total spot diagram can be analyzed as a combination of spot diagrams from the regions. Below we will use ray aberrations and specifically longitudinal ray aberration for describing the invention.

SUMMARY OF THE INVENTION

A lens in accordance with this invention consists of front and back optical surfaces. At least one of the surfaces has at least two regions of different signs of longitudinal ray aberrations.

Image at the retina is represented by a spot diagram and directly characterized by transverse ray aberrations. Due to more complex description of the transverse ray aberration which involves 2-dimensional characterization, it is more illustrative to describe the invention in terms of longitudinal ray aberration which involves 1-dimensional characterization. Optical design programs such as Zemax® Optical Software incorporates graphical representation of longitudinal spherical aberration (LSA) and used for non-prolate aspheric surface explanation.

The invention involves the option that longitudinal ray aberration with one sign dominates at normal photopic condition of medium pupil size of about 3 mm at which the best focus position is defined, and longitudinal ray aberrations of the opposite sign contribute with the pupil dilation from about 3 to about 5 mm at mesopic condition. This is accomplished by the convex surface being flatter the spherical surface of equivalent power up to about 3 mm diameter and then steeper the spherical surface beyond about 3 mm diameter, i.e. the surface shape is non-prolate aspheric design. Generally, the peripheral region may be the region of zero longitudinal ray aberration to accomplish at least some benefits.

As a result, these combination of surface regions creates a compensatory effect on the spot diagram by different signs of the longitudinal ray aberrations from different surface regions at large pupils as light rays distribute in front and behind the best image position defined at about 3 mm pupil. The rays intersection distribution at the optical axis is different in case of prolate aspheric where rays concentrate increasingly in front of the best focus position with the pupil dilation at mesopic condition at lens centered position except if the aberration is fully corrected as in Tecnis® type lens, i.e. the total spot diagram is the integration of the spot diagrams from the different regions.

Thus, a compensatory effect is created by the condition that some rays are intersect optical axis in front of the best focus and some behind the best focus. At photopic pupil 3 mm, the best foci of the eye with spherical, prolate aspheric and non-prolate aspheric lenses are about at the same location because the aberrations are very small. If a spherical lens or prolate lens is in the centered position and the best focus position is defined at photopic pupil of about 3 mm, pupil dilation leads to the spot diagram increase as it is proportional to the amount of longitudinal ray aberrations. Spot diagram doesn't change if the aberrations are fully corrected as in Tecnis® type lens if the lens is in centered position. Spot diagram increases with pupil dilation if the prolate aspheric lens leaves some residual aberration of the eye as in case of AcrySof® and SofPort® types of lenses. The spot diagram is the result of integration or summation of spot diagrams formed by the central and peripheral regions because they have the same sigms of longitudinal ray aberrations. Spherical lens has the largest spot diagram with pupil dilation because the lens contributes the additional aberrations of the same sign as the corneal aberration. In case of non-prolate lens, the spot diagram may stay almost the same size with pupil dilation because longitudinal aberration from the area of the aspheric surface exposed with the dilation at mesopic condition has an opposite sign than from the surface area exposed at photopic pupil thus overlapping the spot diagrams created by central "photopic" region and annulus "mesopic" region of the lens non-prolate aspheric surface. The presence of the longitudinal aberrations of difference signes results in the compensatory effect on the spot diagram, opposite to summation effect on the spot diagram in case of prolate aspheric lens. In general, some benefit also can be achieved to have one of the regions with null longitudinal ray aberration to avoid summation effect of the prolate aspherization.

With the lens misalignment at the optical axis, the spot diagram size formed with prolate aspheric lens asymmetrically expands along the meridional axis of the misalignment because the meridionally opposite regions of the aspheric surface are exposed to the passing light and these opposite surface regions have different contribution to ray aberrations at the image plane. In case of spherical lens, this contribution is relatively small as compared with the aberrations that are independent of lens asymmetry due to misalignment such as defocus and spherical aberration. In case of a prolate aspheric lens, the asymmetric contribution increases with smaller residual aberrations of the eye when lens is in centered position such as defocus and spherical aberration which are independent of lens asymmetry due to misalignment, i.e. asymmetry of the spot diagram is the largest in case of a Tecnis® type lens. The asymmetric contribution is less pronounced as the more defocus and spherical aberrations present, i.e. smaller effect for SofPort® then with AcrySof®. In case of non-prolate aspheric lens, the asymmetric ray aberration contribution is also present with the lens misalignment but only marginally because again longitudinal ray aberrations of different signs at periphery and central regions are involved in forming the spot diagram thus creating some overlap in the spot diagrams from these regions, i.e. a compensatory effect.

The unexpected outcome of the invention is that if longitudinal ray aberrations of different signs are involved with pupil dilation and lens misalignment thus creating a compensatory effect at the spot diagram therefore, providing more effective aspheric surface design to provide the improved image quality.

The described concept of compensatory effect of the ray aberrations with pupil dilation and lens misalignment within realistic clinical condition can be applied not only to Aphakic IOL but to Phakic IOL and Multifocal Diffractive IOL where base profile is at least a part of the total non-prolate aspheric surface profile.

BRIEF DESCRIPTION OF THE DRAWINGS

The advantages and features of the present invention will be better understood by the following description when considered in conjunction with the accompanying drawings in which.

DETAILED DESCRIPTION

Figure 1:
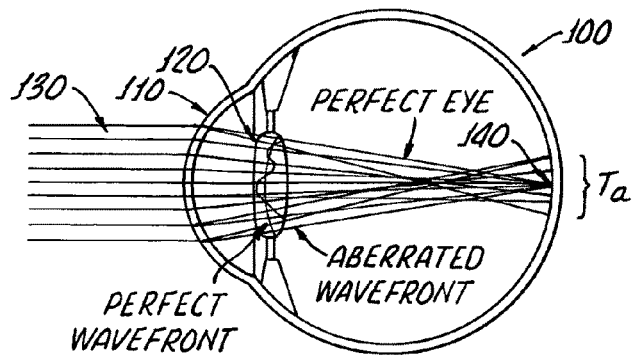
FIG. 1 illustrates the schematic eye with Aphakic IOL shown light beam passing through it and creating aberrated wavefront superimposed over the perfect wavefront.

FIG. 1 illustrates the schematic eye 100 with the IOL 120 inside the eye in place of a natural crystalline lens. The light beam 130 from distant point-object passes though the cornea 110 and lens 120 to form an image at the back of the eye. In case of a perfect optical system the perfect spherical wavefront is formed resulted in a single point focus 140. Commonly, the wavefront is aberrated and the resulted image is spread out within the range $T_a$ forming larger spot diagram thus reducing the image quality of the point-object. The spread of the light can be directly described by transverse ray aberrations of the eye.

Figure 2:
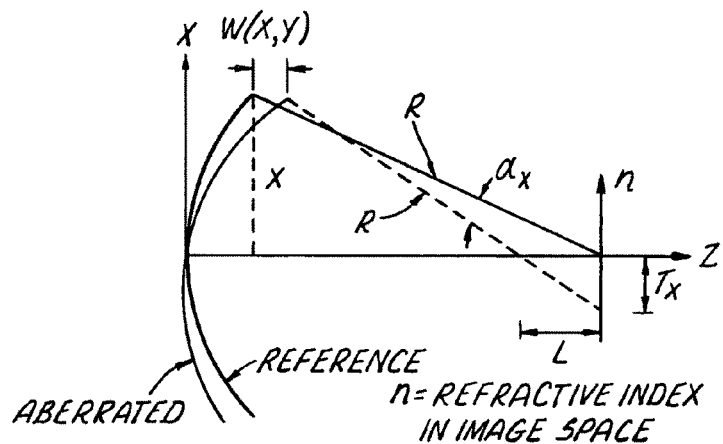
FIG. 2 illustrates aberrated wavefront and perfect wavefront and how it correlates with the ray aberrations

FIG. 2 illustrates aberrated wavefront and perfect wavefront and how it corresponds to ray aberrations. The mathematical relationship was introduced in the Background section above in case of a relatively small magnitude of the aberrations. For instance, longitudinal ray aberration is proportional to the first derivative of the wavefront error:

$$L \sim -\frac{\partial W(x, y)}{\partial x}.$$

Utilizing polar coordinates for wavefront error and Zernike Polynomial Decomposition $W(\rho,\theta)=\Sigma a_{n,m}Z_n^m(\rho,\theta)$, one can determine the relationship between longitudinal ray aberration and set of wavefront aberrations:

$$L \sim -\sum a_{n,m}\frac{\partial Z_n^m(\rho, \theta)}{\partial \rho} \qquad \text{Eq. 1}$$

In the centered optical system all aberrations depending upon the $\theta$-coordinate, so called non-symmetrical aberrations, are zero but with a misalignment these aberrations contribute to the image quality.

Figure 3:
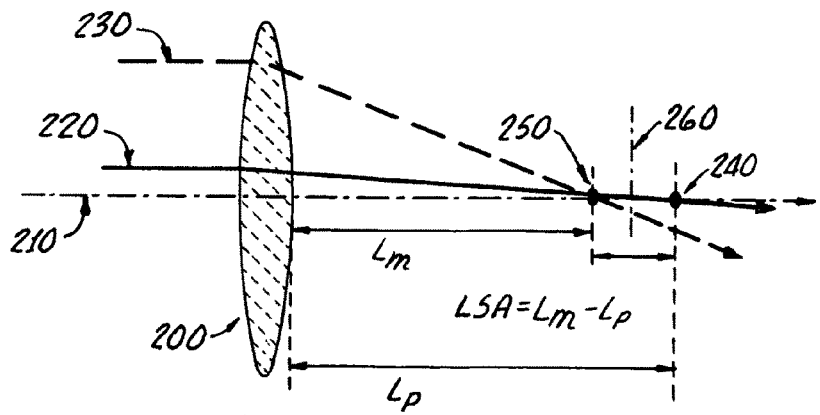
FIG. 3 illustrates lens manifesting longitudinal ray aberration in the case of centered optic system called longitudinal spherical aberration.

FIG. 3 illustrates lens manifesting longitudinal ray aberration in the case of centered spherical optic system 200 over the optical axis 210. More central ray 220 has focal point 240 and more peripheral ray 230 has focal point 250. This is a common manifestation of the foci by a positive spherical lens. Commonly, more central ray manifests minimum aberration and corresponds to the perfect wavefront. As a result, the difference between focal points 250 and 240 represents longitudinal ray aberration. In case of the central ray being paraxial ray and peripheral ray being marginal the corresponding longitudinal ray aberration is called longitudinal spherical aberration, LSA. In this invention the definition of the LSA has been expended to allow characterize individual surface region in terms of LSA defined as a difference in longitudinal aberration of the rays at the edges of the region in lens centered position.

The best focus position is close to the center of the LSA and shown by 260 and the distance to 240 represents defocus in terms of ray aberration. The figure demonstrates that both longitudinal spherical aberration and defocus varies with the aperture. All other aberrations are zero in this centered lens condition. With the lens misalignment other aberrations become non-zero and defocus takes a more complex dependence upon the set of aberrations.

Figure 4:
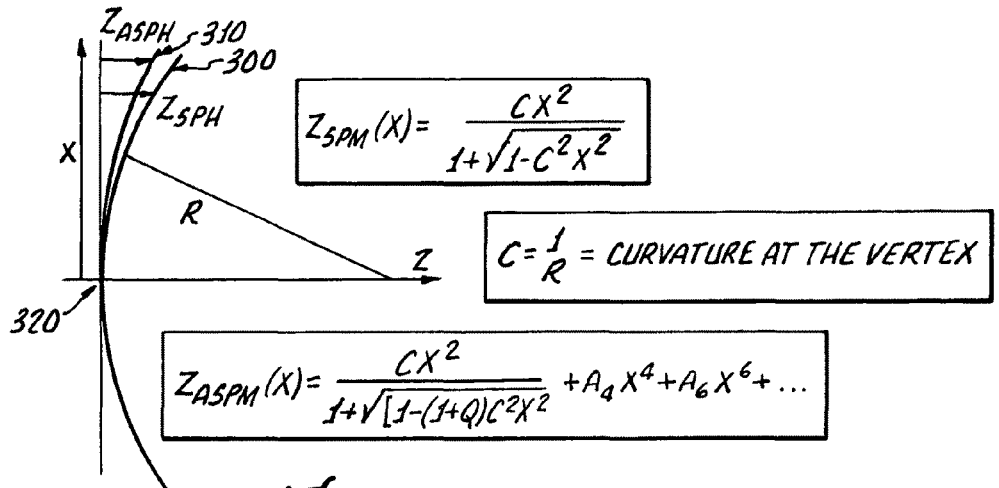
FIG. 4 provides description of spherical and aspheric surfaces

FIG. 4 graphs spherical 300 and aspheric 310 surfaces with the corresponding mathematical descriptions. Aspheric surface includes asphericity Q and aspheric coefficients $A_i$. Both surfaces have the same radial magnitude at the apex or vertex 330. As shown, the surface of the aspheric surface 310 flattens from the corresponding spherical surface 300 with the distance to the surface apex x, i.e. radii are progressively increasing illustrating a typical prolate type aspheric lens of the prior art such as Tecnis®, AcrySof® and SofPort® AO.

Figure 5:
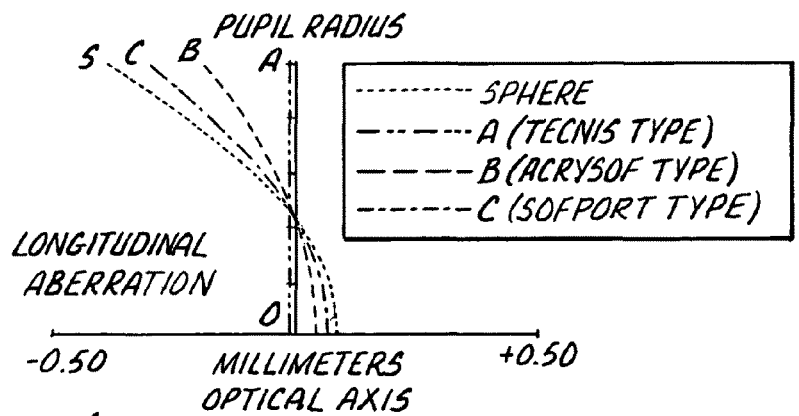
FIG. 5 demonstrates longitudinal aberrations of spherical and prolate type aspherics of prior art.

FIG. 5 demonstrates longitudinal ray aberrations of spherical lens and prolate type aspherics of the prior art in the nominal eye and lens centered position. Graphs are plotted for 5 mm aperture. In this case, longitudinal ray aberration coincides with longitudinal spherical aberration because only spherical aberration and defocus present. The graphs demonstrate that Tecnis® type aspheric, graph A, is designed to fully compensate spherical aberration of the cornea and the corresponding LSA is zero for the full apertures. AcrySof® type design is represented by the graph B, followed by SofPort® AO type design, graph C, and then spherical lens, graph S. One can see, that the negative magnitude of the longitudinal ray aberration is maintained and increases towards the aperture periphery. Assume that either of the above referenced lenses is placed in the eye and ends up with some misalignment within realistic clinical condition. At 3 mm pupil the aberrations are relatively small for all lenses and do not present an imaging issue but with pupil dilation above 4 mm diameter more of the lens surface periphery is exposed to the light beam passing through the lens and additional negative sign longitudinal ray aberration contribute to the lens imaging. In the eye with lens misalignment, the same sign of longitudinal ray aberrations corresponds to the same sign of non-symmetrical aberrations thus resulting in a compounded effect and reduced image quality.

Figure 6:
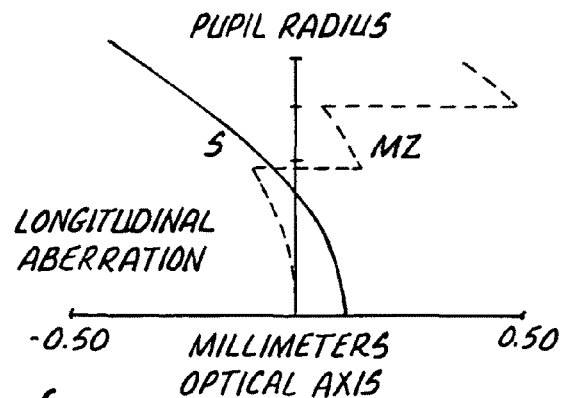
FIG. 6 demonstrates longitudinal aberrations of spherical and multizonal surface of the prior art designed to reduce sensitivity to lens decentration.

FIG. 6 demonstrates longitudinal ray aberrations of spherical S and multizonal surface MZ of the prior art which was designed to reduce sensitivity to lens decentration. The assumption of the design was that the defocus changes with the decentration and zones of prolate aspheric profiles were shifted accordingly. The design partially impact defocus aberration but doesn't provide compensatory effect involved with the change in sign of the ray aberration. In addition, in includes abrupt changes in the surface resulting in potential light scattering.

Figure 7:
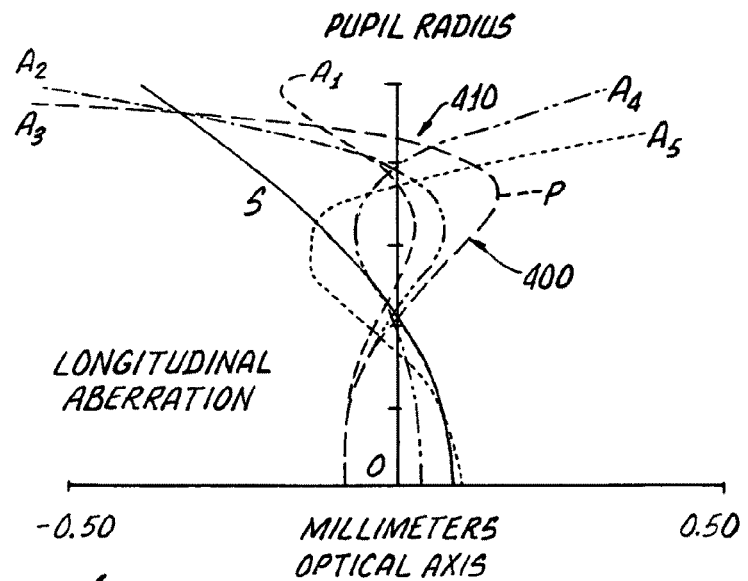
FIG. 7 demonstrates longitudinal aberrations of spherical and non-prolate aspherics of this invention.

FIG. 7 demonstrates longitudinal ray aberrations of spherical and non-prolate aspherics of the present invention. There are several examples of the longitudinal ray aberration graphs of the eye with non-prolate aspheric lenses. Different shapes are preferred for different lens powers and material refractive indices. Graph S represents longitudinal spherical ray aberration of the eye with spherical lens of a middle power. Non-prolate surface designs that produce longitudinal spherical aberration graphs $A_1$, $A_2$ and $A_3$ incorporate positive ray aberration at the central region of the surface of about 3 mm with absolute magnitudes less or similar to spherical lens in order to maintain high image quality for average photopic pupil size. The region of the lens at the periphery produces negative ray aberration in order to introduce a compensatory effect if the periphery of the lens is exposed either due to dilated pupil or lens misalignment or a combination of both. For instance, in case of longitudinal ray aberration $A_3$ is shown to be divided into two parts, the region 400 from 0 to P demonstrating positive ray aberration and region 410 above P incorporates negative ray aberration.

The figure also demonstrates longitudinal ray aberration graphs $A_4$ and $A_5$ with central region having negative ray aberration and periphery with positive ray aberration.

Non-prolate aspheric surface can be incorporated in aphakic IOL, phakic IOL, toric IOL or diffractive multifocal IOL. In later case, it may include base surface as the whole aspheric surface or a portion of non-prolate aspheric surface. For instance, if the diffractive bifocal zone covers the whole surface then the base surface is non-prolate aspheric surface to improve distant image quality for dilated pupil or lens misalignment or a combination of both. If diffractive bifocal zone covered the lens surface only partially, say within about 4 mm central diameter or annulus between about 1.75 mm and 4 mm diameters, then the base surface profile may produce longitudinal ray aberration of one sign and the surface periphery with different sign for longitudinal ray aberration. For instance graph $A_4$, the base curve might even be spherical profile that produces negative longitudinal ray aberration but the peripheral portion produces positive longitudinal ray aberration.

Figure 8:
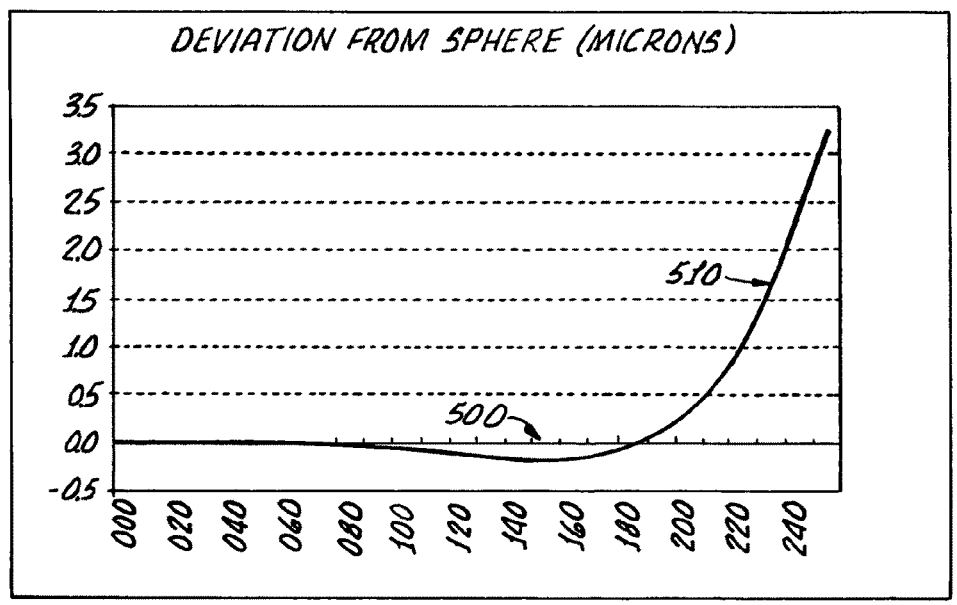
FIG. 8 demonstrates a profile of one of the non-prolate aspheric surfaces of the IOL as deviation from spherical surface.

FIG. 8 demonstrates a non-prolate aspheric surface profile 510 of the non-prolate aspheric IOL corresponding to $A_2$ longitudinal ray aberration of the eye as a deviation from spherical surface 500 of the IOL with the same radius as the vertex radius of non-prolate aspheric surface. The central region of the non-prolate aspheric posterior surface up to about 1.5 mm radius is flatter the corresponding spherical surface and steeper at the surface periphery.

Figure 9:
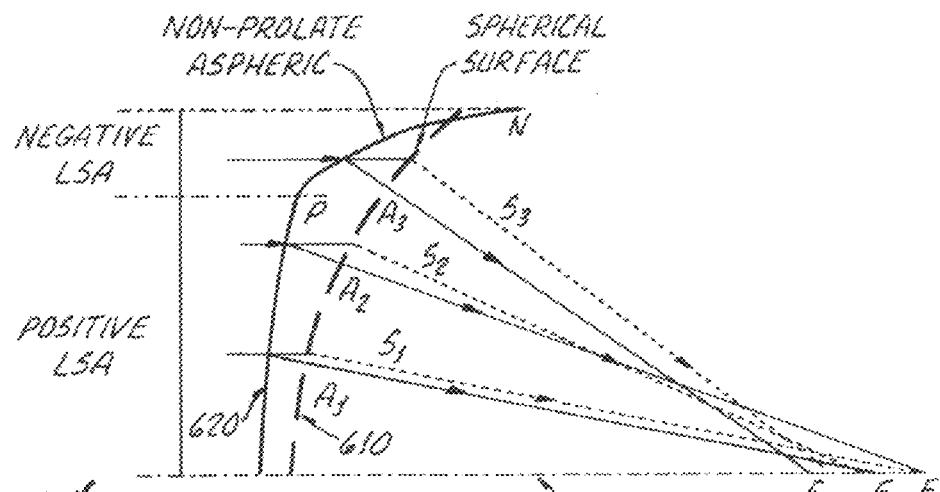
FIG. 9 illustrates longitudinal aberrations of spherical and non-prolate aspheric IOLs and the corresponding surface profiles of the IOLs

FIG. 9 demonstrates spherical 610 and non-prolate aspheric 620 surface profiles of an IOL in accordance with the present invention. More central ray $A_1$ focuses at $F_1$ at the optical axis 600. There are shown two regions though it could more regions producing different signs of longitudinal ray aberration. Central region of non-prolate aspheric surface from 0 to P creates positive longitudinal ray aberration. i.e. ray $A_2$ focused at $F_2$ which is farther away from $F_1$. The size of the central region is about the size of the photopic pupil of about 3 mm diameter. Peripheral region of non-prolate aspheric surface from P to N creates negative longitudinal ray aberration, i.e. ray $A_3$ focused at $F_3$ which is closer to the lens than the focus of the ray passing the surface at point P. The size of the peripheral regions is of annular shape between central region and about 5 mm diameter corresponding to mesopic pupil dimension. The best focus position 260' is defined at photopic condition and is close the middle of the longitudinal ray aberration range formed by the central region OP, i.e. somewhere between $F_1$ and $F_2$. At mesopic condition, both regions are exposed. In general, one of the regions, for instance peripheral region, may have zero longitudinal ray aberration to achieve at least some benefits over the prolate type aspherization.

In case of the positive spherical surface 610 of similar power, the focus $S_1$ starts farther away from the surface and becoming closer to the surface as rays move toward the surface periphery, $S_2$ and $S_3$.

The non-prolate aspheric surface can be placed either on front or back surface of the lens which is optically equivalent. The opposite lens surface can be spherical, toric or multifocal.

As an example, Table 1 below describes the lens with posterior placement of the non-prolate Aspheric 1 corresponding to the Graph $A_1$ of FIG. 7 and Aspheric 2 corresponding to the Graph $A_2$ of the FIG. 7.

TABLE 1

Non-prolate aspheric posterior surface of IOL

| Parameters | Non-Prolate Aspheric 1 (n = 1.489) | Non-Prolate Aspheric 2 (n = 1.461) D |
|---|---|---|
| Front spherical radius R (mm) | 11.75 | 9.54 |
| Back vertex radius $R_v$ (mm) | −27.5(*) | −25.0(*) |
| $A_4$ | 0.00054915888 | −1.0403520E−04 |
| $A_6$ | 0.0003180248 | 3.3590899E−05 |
| $A_8$ | −0.00010754862 | −5.3457486E−07 |
| $A_{10}$ | 9.2178714e−006 | 0 |
| $A_{12}$ | 2.2866778e−007 | 0 |
| $A_{14}$ | −4.0279669e−008 | 0 |

(*)negative radius value for posterior convex surface

Figure 10:
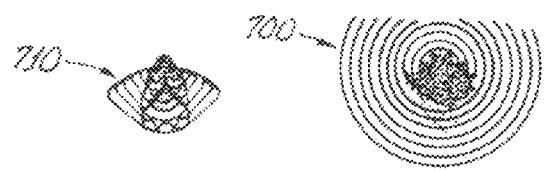
FIG. 10 is a plan view of image spot diagrams formed by the eye with spherical IOL, prolate Tecnis® type IOL and non-prolate aspheric IOL all with 1 mm decentration and at 5 mm pupil
Figure 10:
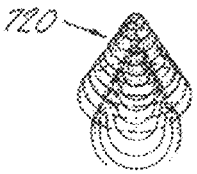

FIG. 10 is a plan view of image spot diagrams formed by the nominal eye with spherical IOL 700, prolate Tecnis® type IOL 720, and non-prolate aspheric IOL 720, all with 1 mm decentration and at 5 mm pupil. Spot diagram is a common way to illustrate the image of a point-object. In this case, distant point-object with spot diagram being its image at the retina. Dots forming each spot diagram represent the rays coming from the distant point-object, passing through the optical system, the eye in this case, and intersecting the retina to form the image of the distant point-object. This is very close simulation of the actual image at the retina by each type of IOL used in the analysis.

The spot diagrams were produced in Zemax® Optical Design Software at the Beat Focus defined at 3 mm pupil for the same 1 mm decentration of each IOL. It is analogous to common condition of IOL power calculation which is conducted for photopic condition, i.e. average pupil of 3 mm. Upon the implantation, the lens may ends up with some misalignment within realistic clinical condition which maintains good image quality at the photopic condition but inhibits it with the pupil dilation at mesopic condition.

Each ray can be characterized by longitudinal aberration related to transverse aberrations at the image plane. The spherical lens spot diagram 700 produces the largest spot size but with no ray overlap demonstrating the dominance of defocus and spherical aberration. The average diameter of the spot corresponds to the amount of defocus. There is a slight asymmetry in the spot diagram 700 at its center indicating small comatic ray aberration.

The spot diagram 720 produced by the prolate Tecnis® type aspheric clearly demonstrates highly asymmetrical spot diagram. The average diameter indicates the amount of defocus and "V" shaped (inverted "V" in this case) tip oriented towards the point corresponding to the central ray indicates significant comatic aberration. The length of the coma type image, length in the vertical direction from the tip dawn, is the measure of tangential coma aberration and it is significant for Tecnis® type prolate aspheric.

The spot diagram 710 produced by non-prolate aspheric surface defined as Aspheric 1 of Table 1. The averaged diameter of the spot size is the smallest, i.e. the smallest defocus. There is some asymmetrical structure in the spot diagram indicating a presence of some coma but its length is substantially smaller than in 720 indicating smaller amount of tangential coma aberration. There is also a signature of different orientations corresponding different signs of ray aberrations at lens center and periphery regions of the lens, graph $A_1$ of the FIG. 7.

As was mentioned in the background section, the RMS of wavefront aberrations provides a measure of relative contributions between LOA that includes defocus and HOA that includes spherical aberration and coma.

TABLE 2

Wavefront Aberrations Analysis

| IOL position in the Eye Model | RMS (μ) | Spherical IOL | Tecnis ® type IOL | Non-Prolate Aspheric |
|---|---|---|---|---|
| 1.0 mm decentration | Total RMS $RMS_{HOA}$ | 0.63 0.26 | 0.91 0.71 | 0.41 0.30 |

Low Order Aberration RMS can be determined by $(RMS_{LOA})^2 = (Total\ RMS)^2 - (RMS_{HOA})^2$. The Table 2 confirms that LOA has the largest contribution, 0.57 micron, then HOA, of 0.26 micron, for spherical lens. Also according to the Table 2, $RMS_{HOA}$ of Tecnis® type lens is the largest which correlates with the largest coma illustrated by the spot diagram of the FIG. 10. As expected, HOA of the non-prolate lens includes slightly higher HOA of the spherical lens but LOA is significantly smaller confirming the smallest size of the non-prolate aspheric spot diagram per the illustration in the FIG. 10.

Figure 11A:
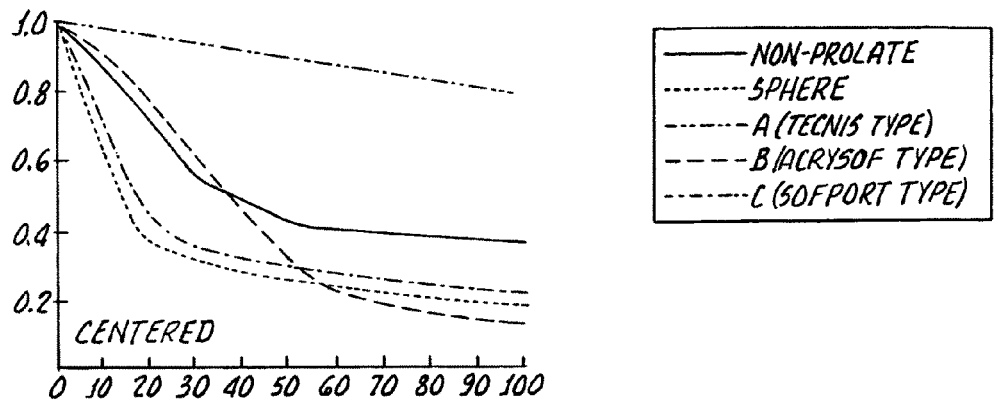
FIGS. 11A, 11B, 11C are examples of Modulation Transfer Functions (MTFs) of the eye with spherical, prolate type aspherics and non-prolate aspheric at centered lens position and lens misalignments all at dilated 5 mm pupil with best focus defined at 3 mm pupil.
Figure 11B:
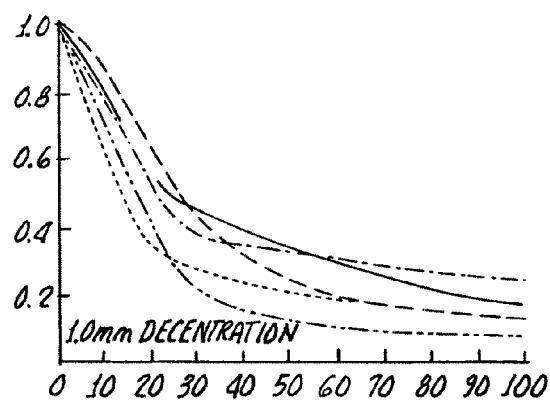
Figure 11C:
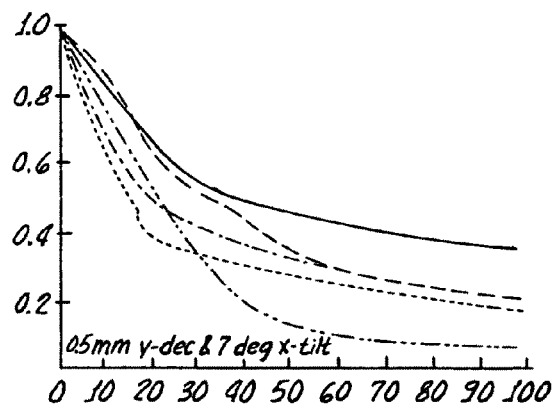

FIGS. 11A, 11B and 11C demonstrate graphs comparing Modulation Transfer Functions (MTFs) of the eye with spherical, prolate type aspherics (Tecnis®, AcrySoft® and SofPort® AO types lenses) and non-prolate aspheric at centered lens position, FIG. 11A, 1 mm decentration, FIG. 11B, and 0.5 mm decentration combined with 7 degrees tilt, FIG. 11C. The graphs were calculated theoretically by Zemax® Optical Program and analogous to image contrast if the corresponding IOL is implanted into a real eye. The Best Focus at each lens position was defined at 3 mm pupil corresponding to photopic condition and the MTFs were calculated at 5 mm pupil without adjusting the focus position. 5 mm pupil corresponds to mesopic condition. The MTF graphs demonstrate that Tecnis® type lens is the most sensitive to lens misalignment, it is the largest at the lens centered position but drop significantly with the misalignment. SofPort® AO type is better spherical lens for all condition but only slightly. AcrySof® is somewhere in between but non-prolate Aspheric demonstrate significant improvement over spherical and improvement over prolate lenses of the prior art for realistic clinical condition.

Figure 12:
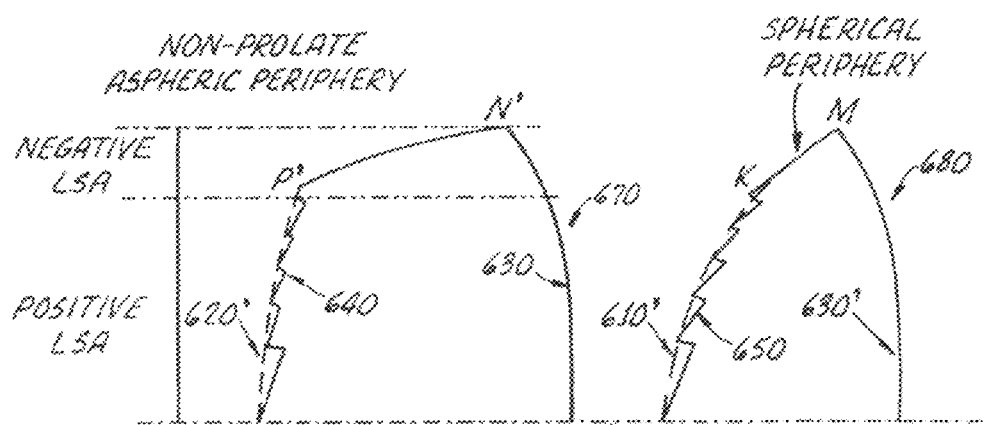
FIG. 12 demonstrates diffractive multifocal IOL with spherical base surface and its spherical periphery and diffractive multifocal IOL with non-prolate front surface as the combination of base surface and its periphery.

FIG. 12 demonstrates diffractive multifocal IOL 660 with spherical base surface 610' between LK and its spherical periphery KM and diffractive multifocal IOL with non-prolate front surface as the combination of base surface 620' between 0'P' and its aspheric periphery P'N'. For illustration purpose, each combination of base surface and its periphery is shaped the same as the corresponding surface of FIG. 9 where non-prolate and spherical surfaces were shown. The longitudinal spherical aberration of the base surface 0'P is shown as positive with the periphery P'N, producing negative longitudinal spherical aberration. The exact split between the regions of positive and negative longitudinal spherical aberration may vary from the above illustration as base surface itself may be a combination of the regions with different signs of longitudinal spherical aberrations.

The diffractive echelettes 640 are superimposed on aspheric base surface 620' which firms non-prolate aspheric by itself or in combination with the periphery P'N' in case of IOL 660 and diffractive echelettes 650 are superimposed on the spherical base 610'. The back surface of lens 670 is surface 630 and back surface of lens 660 is surface 630' which are substantially spherical surfaces of similar power in order for lens 660 and lens 670 to have essentially similar powers for distance. Illustration on FIG. 12 demonstrates muiltifocal surface occupying only central part of the front surface but it can occupy the whole surface, so called full surface diffractive multifocal. In that case, the base surface of the full surface diffractive multifocal can be non-prolate aspheric surface.

The diffractive zone may also occupy the annulus of the multifocal surface with small central refractive zone of not more than about 2 mm diameter to enhance distance vision of the multifocal lens. The base surface of the corresponding diffractive annulus zone can have non-prolate aspheric profile or be a region of non-prolate aspheric surface that includes the surface periphery.

Multifocal surface can also be placed on the back as the inventions can be applied to either the surfaces which is optically equivalent. In general, non-prolate aspheric surface with base surface being whole or region of the multifocal surface and may have more than 2 regions providing different signs of longitudinal ray aberration Although there has been hereinabove described a specific non-prolate aspheric intraocular lens in accordance with the present invention for the purpose of illustrating the manner in which the invention may be used to advantage, it should be appreciated that the invention is not limited thereto. That is, the present invention may suitably comprise, consist of, or consist essentially of the recited elements. Further, the invention illustratively disclosed herein suitably may be practiced in the absence of any element which is not specifically disclosed herein. Accordingly, any and all modifications, variations or equivalent arrangements which may occur to those skilled in the art, should be considered to be within the scope of the present invention as defined in the appended claims.

What is claimed is:

1. An optic comprising an intraocular lens having a front and a back surface, at least one of the front and back surfaces comprising a continuous non-prolate aspheric surface with at least two regions, a peripheral region and a central region, the peripheral region of the optic being configured for producing a peripheral region longitudinal ray aberration, the central region of the optic being configured for producing a central region longitudinal ray aberration, the peripheral region longitudinal ray aberration being of a different sign than the central region ray aberration, wherein the central region is inside the peripheral region and where the peripheral region is inside a 5 mm diameter.

2. The optic according to claim 1 wherein the central region is annular.

3. The optic according to claim 1 wherein the continuous non-prolate aspheric surface extends from an optical axis of the lens to create a positive longitudinal ray aberration at the central region and the peripheral region of the non-prolate aspheric aspheric surface creates a negative longitudinal ray aberration.

4. The optic according to claim 3 wherein the central region has a diameter of about 3 mm.

5. The optic according to claim 1 wherein the continuous non-prolate aspheric surface extends from an optical axis of the lens to create a negative longitudinal ray aberration at the central region and the peripheral region of the non-prolate aspheric surface creates a positive longitudinal ray aberration.

6. The optic according to claim 5 wherein the central region has a diameter of about 3 mm.

7. The optic according to claim 1 wherein the peripheral region comprises a steeper curvature as compared to a spherical surface and wherein the central region comprises a flatter curvature as compared to the spherical surface.

8. The optic according to claim 1 wherein said intraocular lens comprises a phakic intraocular lens.

9. The optic according to claim 1 wherein said intraocular lens comprises a toric intraocular lens.

10. The optic according to claim 1 wherein said intraocular lens comprises a diffractive multifocal intraocular lens with non-prolate aspheric surface for image of the lens.

11. The optic according to claim 10, wherein the peripheral region comprises a steeper curvature as compared to a spherical base surface and wherein the central region comprises a flatter curvature as compared to the spherical base surface.

12. The optic according to claim 1 wherein the intraocular lens is selected from a group consisting of an aphakic intraocular lens, a phakic intraocular lens, a toric intraocular lens and a diffractive multi-focal intraocular lens.

13. The optic according to claim 1, wherein the intraocular lens comprises a multifocal diffractive surface having a non-prolate aspheric base surface.

14. A method for producing an aspheric optic with minimized effect on image quality by lens misalignment occurred clinically:
providing an intraocular lens having a front surface and a back surface;
shaping one of either the front surface and back surface with at least two regions, each region configured for producing a different sign of longitudinal ray aberration of each region, wherein the at least two regions comprise a peripheral region and a central region, the peripheral region of the aspheric optic being configured for producing a peripheral region longitudinal ray aberration and the central region of the optic being configured for producing a central region longitudinal ray aberration, wherein the central region is inside the peripheral region and where the peripheral region is inside a 5 mm diameter.

15. The method according to claim 14 wherein the peripheral region comprises a steeper curvature as compared to a spherical surface and wherein the central region comprises a flatter curvature as compared to the spherical surface.

16. The optic according to claim 1 wherein an absolute magnitude of the longitudinal spherical aberration of the central region is about the same as an absolute magnitude of a longitudinal spherical aberration produced by a spherical lens of equivalent power and by an equivalent central region size.

17. The method according to claim 14 wherein the central region with the longitudinal spherical aberration comprises an absolute magnitude equivalent to an absolute magnitude of a spherical lens of equivalent power and by an equivalent central region size.

18. The method according to claim 14 wherein the shaping of one of the regions includes forming the one region as a base surface of a diffractive multifocal lens.

19. The method according to claim 14, wherein the intraocular lens comprises a multifocal diffractive surface having a non-prolate aspheric base surface.

20. An intraocular lens, comprising:
a front and a back surface;
wherein either the front or back surface comprises a continuous non-prolate aspheric surface with at least two regions;
wherein the at least two regions comprise a peripheral region surface and a central region surface, where the central region is inside the peripheral region and where the peripheral region is inside a 5 mm diameter;
wherein the peripheral region surface of the optic is configured for producing a peripheral region longitudinal ray aberration by having a steeper curvature as compared to a spherical surface;
wherein the central region surface of the optic is configured for producing a central region longitudinal ray aberration by having a flatter curvature as compared to the spherical surface; and
wherein the peripheral region longitudinal ray aberration is of a different sign than the central region ray aberration.

21. The lens according to claim 20, wherein the central region surface comprises a multifocal diffractive surface.

* * * * *